United States Patent [19]

Hoelderich et al.

[11] Patent Number: 5,196,571
[45] Date of Patent: Mar. 23, 1993

[54] PREPARATION OF UNSATURATED MONOESTERS

[75] Inventors: Wolfgang Hoelderich, Frankenthal; Hardo Siegel, Speyer, both of Fed. Rep. of Germany

[73] Assignee: BASF Aktiengesellschaft, Ludwigshafen, Fed. Rep. of Germany

[21] Appl. No.: 815,649

[22] Filed: Dec. 30, 1991

Related U.S. Application Data

[63] Continuation of Ser. No. 595,693, Oct. 5, 1990, abandoned, which is a continuation of Ser. No. 257,012, Oct. 13, 1988, abandoned.

[30] Foreign Application Priority Data

Oct. 22, 1987 [DE] Fed. Rep. of Germany ....... 3735755

[51] Int. Cl.$^5$ .................................. C07C 67/02
[52] U.S. Cl. ........................ 560/261; 554/31; 554/32; 554/125
[58] Field of Search ............... 560/261; 260/405.5; 554/31, 32, 125

[56] References Cited

U.S. PATENT DOCUMENTS

| 2,901,506 | 8/1959 | Bullock et al. ............... 560/261 |
| 2,941,011 | 6/1960 | Hagemeyer, Jr. et al. ...... 560/261 |
| 3,300,455 | 1/1967 | Gervasi et al. ............... 560/261 |

FOREIGN PATENT DOCUMENTS

| 766147 | 4/1971 | Belgium . |
| 494741 | 7/1953 | Canada ............................ 560/261 |
| 1024496 | 2/1958 | Fed. Rep. of Germany ...... 560/261 |
| 2732075 | 2/1979 | Fed. Rep. of Germany . |

OTHER PUBLICATIONS

Grant, J. (editor), Hackh's Chemical Dictionary 4th edition, McGraw-Hill, N.Y., 1969, p. 684.
Merriam-Webster, Webster's Ninth New Collegiate Dictionary, Merriam-Webster Inc., Springfield, Mass., U.S.A., 1983, p. 884.
Morris, Wm., Editor, The American Heritage Dictionary of the English Language, Houghton Mifflin Co., Boston, 1976, p. 986.
J. Polym. Sci. Polym. Chem. 18 (1980) 1729-1758.

*Primary Examiner*—Arthur C. Prescott
*Attorney, Agent, or Firm*—Keil & Weinkauf

[57] ABSTRACT

Unsaturated monoesters of the formula (I)

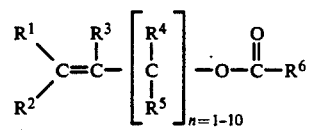

are prepared from diesters of the formula (II)

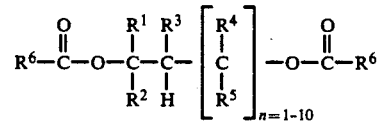

where the radicals $R^1$ to $R^5$ in the formulae (I) and (II) are identical to each other and each is hydrogen, straight-chain or branched alkyl or alkenyl of from 1 to 10 carbon atoms, cycloalkyl or cycloalkylene of from 5 to 8 carbon atoms, aryl, alkylaryl or aralkyl, by reaction in the presence of a zeolite and/or phosphate as a catalyst with the elimination of a carboxylic acid $R^6COOH$ where $R^6$ is hydrogen or alkyl of from 1 to 6 carbon atoms, n being an integer from 1 to 10.

9 Claims, No Drawings

PREPARATION OF UNSATURATED MONOESTERS

Thus application is a continuation of application Ser. No. 07/595,693, filed on Oct. 5, 1990 now abandoned, which is a continuation of Ser. No. 07/257,012 filed on Oct. 13, 1988 now abandoned.

The present invention relates to a process for preparing an unsaturated monoester by eliminating a carboxylic acid from a diester in the presence of a catalyst.

It is known that the pyrolysis of acetoxylated 1,4-butanediols at 525° C. gives butadiene, but that the reaction does not stop at the unsaturated monoacetate (J. Polym. Sci. Polym. Chem. 18 (1980) 1729–1758). BE 766,147 discloses that unsaturated acetates can be prepared by pyrolytic elimination of a carboxylic acid from a glycol acetate, but this pyrolysis is unselective.

We have found a process for preparing an unsaturated monoester of the formula (I)

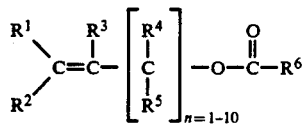

by reacting a diester of the formula (II)

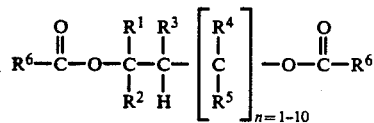

where the radicals $R^1$ to $R^5$ in the formulae (I) and (II) are identical to each other and each is hydrogen, straight-chain or branched alkyl or alkenyl of from 1 to 10 carbon atoms, cycloalkyl or cycloalkylene of from 5 to 8 carbon atoms, aryl, alkylaryl or aralkyl, in the presence of a zeolite and/or phosphate as a catalyst with the elimination of a carboxylic acid $R^6COOH$ where $R^6$ is hydrogen or alkyl of from 1 to 6 carbon atoms. n is an integer from 1 to 10.

Radicals $R^1$ to $R^6$ are hydrogen and straight-chain or branched alkyl or alkenyl of from 1 to 10, preferably of from 1 to 4, carbon atoms.

Alkyl radicals are for example methyl, ethyl, propyl, n-butyl, i-butyl, pentyl, hexyl, octyl or decyl. Alkenyl is for example propenyl, butenyl, hexenyl or octenyl.

Cycloalkyls $R^1$ to $R^5$ are for example cyclopentyl, cyclohexyl, cycloheptyl, cyclopentenyl and cyclohexenyl.

Aromatic radicals $R^1$ to $R^5$ are for example phenyl, benzyl, tolyl, phenylethyl, p-methylbenzyl or p-propylphenyl.

$R^6$ is for example hydrogen, ethyl, propyl, butyl or hexyl.

The catalysts used for the process according to the invention are zeolites and/or phosphates. Zeolites are crystalline aluminosilicates which have a highly ordered structure comprising a rigid three-dimensional network of $SiO_4$ and $AlO_4$ tetrahedra linked by common oxygen atoms. The ratio of the Si and Al atoms:oxygen is 1:2 (see Ullmann's Encyclopädie der technischen Chemie, 4th edition, volume 24, page 575 (1983)). The electrovalence of the aluminum-containing tetrahedra is balanced by the inclusion of cations, for example an alkali metal or hydrogen ion, in the crystal. Cation exchange is possible. The spaces between the tetrahedra are occupied by water molecules prior to dehydration through drying or calcination.

Zeolites are usually used in the acidic form. In zeolites, the aluminum in the lattice may also be replaced by other elements, such as B, Ga, Fe, Cr, V, As, Sb, Bi or Be, or mixtures thereof, or the silicon may be replaced by another tetravalent element such as Ge, Ti, Zr or Hf.

According to their structure, zeolites are divided into various groups. For instance, the zeolite structure in the mordenite group is formed by tetrahedra arranged in chains and in the chabasite group by tetrahedra arranged in layers, while in the faujasite group the tetrahedra form polyhedra, for example in the form of a cuboctahedron which is composed of tetragons and hexagons. Depending on the way the cuboctahedra are linked, which produces differently sized voids and pores, zeolites are classed as type A, L, X or Y.

Catalysts suitable for the process according to the invention are zeolites of the mordenite group or narrow-pored zeolites of the erionite or chabasite type or zeolites of the faujasite type for example Y-, X- or L-zeolites. These groups of zeolites also include the ultrastable zeolites of the faujasite type, i.e. dealuminized zeolites. Methods for preparing such zeolites are described in Catalysis by Zeolites volume 5 of Studies in Surface Science and Catalysis ed. B. Imelik et al. Elsevier Scientific Publishing Comp. 1980, page 203, and Crystal Structure of Ultra-stable Faujasites, Advances in Chemistry Series No. 101, American Chemical Society Washington DC, pages 226 ff (1971), and in U.S. Pat. No. 4,512,961.

It is particularly advantageous to use zeolites of the pentasil type. Their common feature is a pentagon composed of $SiO_4$ tetrahedra. They are characterized by a high $SiO_2/Al_2O_3$ ratio and by pore sizes between those of zeolites of type A and those of type X or Y.

These zeolites can have different chemical compositions. They can be aluminosilicate, borosilicate or iron, beryllium, gallium, chromium, arsenic, antimony or bismuth silicate zeolites or mixtures thereof and aluminogerminate, borogerminate and gallium or iron germinate zeolites or mixtures thereof. Particularly suitable for the process according to the invention are the aluminosilicate, borosilicate and iron silicate zeolites of the pentasil type. The aluminosilicate zeolite is prepared for example from an aluminum compound, preferably $Al(OH)_3$ or $Al_2(SO_4)_3$, and a silicon component, preferably finely divided silicon dioxide, in an aqueous amine solution, in particular in polyamines such as 1,6-hexanediamine or 1,3-propanediamine or triethylenetetramine solution, in the presence or in particular in the absence of alkali or alkaline earth metal at from 100° to 220° C. under autogenous pressure. This also includes the isotactic zeolites described in EP 34,727 and EP 46,504. The aluminosilicate zeolites obtained have an $SiO_2/Al_2O_3$ ratio of from 10 to 40,000, depending on the mixing ratio of the starting materials. Such aluminosilicate zeolites can also be synthesized in an ether medium such as diethylene glycol dimethyl ether, in an alcohol medium such as methanol or 1,4-butanediol, or in water.

Borosilicate zeolites are synthesized under autogenous pressure, for example at from 90° to 200° C., by reacting a boron compound, for example $H_3BO_3$, with a silicon compound, preferably finely divided silicon dioxide, in an aqueous amine solution, in particular in 1,6-hexanediamine, 1,3-propanediamine or triethylenetetramine solution, in the presence or in particular in the absence of alkali or alkaline earth metal. They also include the isotactic zeolites described in EP 34,727 and EP 46,504. These borosilicate zeolites can also be prepared by carrying out the reaction not in an aqueous amine solution but alternatively in an ether solution, for example diethylene glycol dimethyl ether, or in an alcohol solution, for example 1,6-hexanediol.

Iron silicate zeolites are obtained for example from an iron compound, preferably $Fe_2(SO_4)_3$, and a silicon compound, preferably finely divided silicon dioxide, in an aqueous amine solution, in particular 1,6-hexanediamine, in the presence or absence of alkali or alkaline earth metal at from 100° to 220° C. under autogenous pressure.

The high-silicon zeolites usable according to the invention ($SiO_2/Al_2O_3 \geq 10$) also include the various ZSM types, ferrierite, NU-1 and Silicalit®, a silica polymorph molecular sieve.

The aluminosilicate, borosilicate and iron silicate zeolites thus prepared, after they have been isolated, dried at from 100° to 160° C., preferably at 110° C., and calcined at from 450° to 550° C., preferably at 500° C., can be combined with a binder in a ratio of from 90:10 to 40:60% by weight and molded into extrudates or tablets. Suitable binders are various aluminum oxides, preferably boehmite, amorphous aluminosilicates having an $SiO_2/Al_2O_3$ ratio of from 25:75 to 90:5, preferably 75:25, silicon dioxide, preferably finely divided $SiO_2$, mixtures of finely divided $SiO_2$ and finely divided $Al_2O_3$, $TiO_2$, $ZrO_2$, and clay. After molding, the extrudates or tablets are dried at 110° C./16 h and calcined at 500° C./16 h.

It is also possible to obtain advantageous catalysts by molding the isolated aluminosilicate or borosilicate zeolite immediately after drying and subjecting it to calcination only after the molding. The aluminosilicate and borosilicate zeolites prepared can be used in the pure form, without binder, as extrudates or tablets, the extrusion or peptization aids used being for example ethylcellulose, stearic acid, potato starch, formic acid, oxalic acid, acetic acid, nitric acid, ammonia, amines, silicoesters and graphite or mixtures thereof.

If the zeolite, on account of its manner of preparation, is present not in the catalytically active, acidic H-form but, for example, in the Na-form, it can be completely or partially converted into the desired H-form by ion exchange, for example with ammonium ions and subsequent calcination, or by treatment with acids.

Should the zeolitic catalyst used according to the invention undergo deactivation due to coking, it is advisable to regenerate the zeolite by burning off the coke deposit with air or with an air/$N_2$ mixture at from 400° to 500° C., preferably at 500° C. This restores the initial activity level of the zeolite.

By precoking it is possible to set the activity of the catalyst for optimum selectivity in respect of the desired reaction product.

To obtain a high selectivity, high conversions and long times on stream, it is advantageous to modify the zeolites. A suitable method of modifying the catalysts comprises for example doping the molded or unmolded zeolite with metal salts by ion exchange or impregnation. The metals used are alkali metals such as Li, Cs or K, alkaline earth metals such as Mg, Ca or Sr, metals of main groups III, IV and V, such as Al, Ga, Ge, Sn, Pb or Bi, transition metals of subgroups IV–VIII, such as Ti, Zr, V, Nb, Cr, Mo, W, Mn, Re, Fe, Ru, Os, Co, Rh, Sr, Ni, Pd or Pt, transition metals of secondary groups I or II, such as Cu, Ag or Zn, and rare earth metals such as La, Ce, Pr, Nd, Fr, Yb or U.

Advantageously, doping is carried out by introducing the molded zeolite into a riser pipe and passing an aqueous or ammoniacal solution of a halide or nitrate of one of the abovementioned metals over it at from 20° to 100° C. Such an ion exchange can take place with the hydrogen, ammonium, or alkali metal form of the zeolite. Another way of applying metal to the zeolite comprises impregnating the zeolitic material with, for example, a halide, nitrate or oxide of one of the abovementioned metals in aqueous, alcoholic or ammoniacal solution. Both ion exchange and impregnation are followed by at least one drying step, optionally by repeated calcination.

A possible embodiment comprises for example dissolving $Cu(NO_3)_2 \times 3\ H_2O$ or $Ni(NO_3)_2 \times 6\ H_2O$ or $Ce(NO_3)_3 \times 6\ H_2O$ or $La(NO_3)_3 \times 6\ H_2O$ or $Cs_2CO_3$ in water and impregnating the molded or unmolded zeolite with this solution for a certain period, for example 30 minutes. Any supernatent solution is stripped of water in a rotary evaporator. The impregnated zeolite is then dried at about 150° C. and calcined at about 550° C. This impregnating step can be carried out repeatedly in succession until the desired metal content is obtained.

It is also possible to prepare an aqueous $Ni(NO_3)_2$ solution or ammoniacal $Pd(NO_3)_2$ solution and to suspend the pure pulverulent zeolite therein at from 40° to 100° C. by stirring for about 24 hours. After filtration, drying at about 150° C. and calcination at about 500° C., the zeolitic material thus obtained can be further processed with or without binders into extrudates, pellets or fluidizable material.

An ion exchange on the zeolite peresent in the H-form of ammonium form or alkali metal form can be carried out by introducing the zeolite in extruded or pellet form into a column and for example passing an aqueous $Ni(NO_3)_2$ solution or ammonical $Pd(NO_3)_2$ solution over it in a recycle loop and at slightly elevated temperatures of from 30° to 80° C. for from 15 to 20 hours. This is followed by washing out with water, drying at about 150° C. and calcination at about 550° C. With some metal-doped zeolites, for example Pd-, Cu- or Ni-doped zeolites, an aftertreatment with hydrogen is advantageous.

A further method of modifying the zeolite comprises treating the zeolitic material, which may be in molded or unmolded form, with an acid such as hydrochloric acid, hydrofluoric acid or phosphoric acid and/or steam, advantageously, for example, by treating the zeolite in pulverulent form with 1N phosphoric acid at 80° C. for 1 hour and then washing with water and drying at 110° C. for 16 hours and calcining at 500° C. in 20 hours. Alternatively, before or after being molded together with a binder, the zeolite is treated for example at from 60° to 80° C. with from 3 to 25% strength by weight, in particular from 12 to 20% strength by weight, aqueous hydrochloric acid for from 1 to 3 hours. Afterwards, the zeolite thus treated is washed with water, dried and calcined at from 400° C. to 500° C.

In a particular embodiment, the acid treatment comprises treating the zeolitic material, before it is molded, with 0.001N to 2N, preferably 0.05N to 0.5N, hydrofluoric acid at elevated temperatures by refluxing for from 0.5 to 5, preferably from 1 to 3, hours. After the zeolitic material has been isolated by filtering and washing, it is advantageously dried at from 100° to 160° C. and calcined at from 450° C. to 600° C. In a further preferred form of the acid treatment, the zeolitic material, after it has been molded together with a binder, is treated at elevated temperatures, advantageously at from 50° to 90° C., preferably at from 60° to 80° C., for from 0.5 to 5 hours with, preferably, from 12 to 20% strength by weight hydrochloric acid. The zeolitic material is subsequently washed and expediently dried at from 100° to 160° C. and calcined at from 450° to 600° C. An HF treatment can also be followed by an HCl treatment.

In another procedure, zeolites can be modified by applying phosphorus compounds, such as trimethoxyphosphate, trimethoxyphosphine or primary, secondary or tertiary sodium phosphate. To this end, the zeolites are impregnated in extruded, tablet or fluidizable form with aqueous $H_3PO_4$ solution, dried at 110° C. and calcined at 500° C.

Further catalysts for the process according to the invention are a phosphate of element B, Al, Zr, Ce, Fe or Sr or a mixture thereof, in particular aluminum phosphates, silicon aluminum phosphates, silicon iron aluminum phosphates, cerium phosphate, zirconium phosphates, boron phosphate, iron phosphate or mixtures thereof.

The aluminum phosphate catalysts used for the process according to the invention are in particular those aluminum phosphates which have been synthesized under hydrothermal conditions and have a zeolite structure.

Hydrothermally synthesized aluminum phosphates are for example APO-5, APO-9, APO-11, APO-12, APO-14, APO-21, APO-25, APO-31 and APO-33. Syntheses of these compounds are described in EP 132,708, U.S. Pat. No. 4,310,440 and U.S. Pat. No. 4,473,663.

For instance, $ALPO_4$-5 (APO-5) is synthesized by preparing a homogeneous mixture of orthophosphoric acid with pseudoboehmite (Catapal SB®) in water, adding tetrapropylammonium hydroxide and then heating at about 150° C. under autogenous pressure in an autoclave for from 20 to 60 hours. The $ALPO_4$ is filtered off, dried at from 100° to 160° C. and calcined at from 450° to 550° C.

$ALPO_4$-9 (APO-9) is likewise synthesized from orthophosphoric acid and pseudoboehmite but in an aqueous DABCO solution (1,4-diazabicyclo[2.2.2]octane) at about 200° C. under autogenous pressure in the course of from 200 to 400 hours.

$ALPO_4$-21 (APO-21) is synthesized from orthophosphoric acid and pseudoboehmite in an aqueous pyrrolidone solution at from 150° to 200° C. under autogenous pressure in the course of from 50 to 200 hours.

Silicon aluminum phosphates suitable for the process according to the invention are for example SAPO-5, SAPO-11, SAPO-31 and SAPO-34. The synthesis of this compound is described in EP Patent 103,117 and U.S. Pat. No. 4,440,871. SAPOs are prepared by crystallization from an aqueous mixture at from 100° to 250° C. under autogenous pressure in the course of from 2 hours to 2 weeks during which the reaction mixture comprising a silicon, aluminum and phosphorus component is converted into aqueous organoamine solutions.

SAPO-5, for example, is obtained by mixing a suspension of $SiO_2$ in aqueous tetrapropylammonium hydroxide solution with an aqueous suspension of pseudoboehmite and orthophosphoric acid and subsequent reaction at from 150° to 200° C. under autogenous pressure in a stirred autoclave for from 20 to 200 hours. After the powder has been filtered off, it is dried at from 110° to 160° C. and calcined at from 450° to 550° C.

Suitable phosphate catalysts for the process also include precipitated aluminum phosphates. Such an aluminum phosphate is prepared for example by dissolving 92 g of diammonium hydrogenphosphate in 700 ml of water. 260 g of $Al(NO_3)_2 \times H_2O$ in 700 ml of water are added dropwise in the course of 2 hours during which pH 8 is maintained by the simultaneous addition of 25% strength $NH_3$ solution. The resulting precipitate is subsequently stirred for 12 hours and then filtered off with suction and washed. It is dried at 60° C./16 h.

Boron phosphates for the process according to the invention are preparable for example by mixing and kneading concentrated boric acid and phosphoric acid and by subsequent drying and calcination in inert gas, air or steam atmosphere at from 250° to 650° C., in particular at from 300° to 500° C.

These phosphates may be modified by impregnation (saturation or spraying) or in some cases even by ion exchange with modifying components as described above for zeolites. As with the zeolite catalysts, a modification with an acid is also possible.

The catalysts described here can optionally be used in the form of from 2 to 4 mm extrudates or as tablets from 3 to 5 mm in diameter or as chips having particle sizes of from 0.1 to 0.5 mm, or in a fluidizable form.

The process according to the invention is preferably carried in the gas phase at from 100° to 500° C., in particular at from 200° to 400° C., under a weight hourly space velocity (WHSV) of from 0.1 to 20 $h^{-1}$, in particular from 0.5 to 5 $h^{-1}$ (g of starting material per g of catalyst per hour). The reaction can be carried out in a fixed bed or else in a fluidized bed.

It is also possible to carry out the reaction at from 50° to 200° C. in the liquid phase (suspension, trickle-bed or liquid phase procedure).

The process can be carried out batchwise but preferably continuously under atmospheric, reduced or superatmospheric pressure.

Involatile or solid starting materials are used in a dissolved form, for example in THF, toluene or petroleum ether solution. In general, the starting materials are diluted with solvents or with inert gases, such as $N_2$, Ar or $H_2O$ vapor. In particular cases it is also possible to use $O_2$.

After the reaction the products are isolated from the reaction mixture in a conventional manner, for example by distillation; unconverted starting materials are if appropriate recycled into the reaction.

It is advisable to separate the gaseous reaction products immediately into the individual components. The separation may be carried out for example in a fractionating column.

EXAMPLES 1–19

The reactions in the gas phase are carried out under isothermal conditions in a tubular reactor (coil, internal diameter 0.6 cm, length 90 cm) for not less than 6 hours. The reaction products are separated off and characterized in a conventional manner. Quantitative determination of reaction products and starting materials is by gas chromatography.

The catalysts used for the process according to the invention are:

Catalyst A

The borosilicate zeolite of the pentasil type is prepared in a hydrothermal synthesis from 640 g of finely divided $SiO_2$, 122 g of $H_3BO_3$ and 8,000 g of an aqueous 1,6-hexanediamine solution (mixture 50:50% by weight) at 170° C. under autogenous pressure in a stirred autoclave. After filtering and washing, the crystalline reaction product is dried at 100° C./24 h and calcined at 500° C./24 h. This borosilicate zeolite comprises 94.2% by weight of $SiO_2$ and 2.3% by weight of $B_2O_3$.

This material is molded with a molding aid into 2 mm extrudates which are dried at 110° C./16 h and calcined at 500° C./24 h.

Catalyst B

Catalyst B is obtained by molding the borosilicate zeolite of Catalyst A with boehmite in a weight ratio of 60:40 into 2 mm extrudates, drying at 110° C./16 h and calcining at 500° C./24 h.

Catalyst C

An aluminosilicate zeolite of the pentasil type is prepared under hydrothermal conditions and autogenous pressure at 150° C. from 65 g of finely divided $SiO_2$, 20.3 g of $Al_2(SO_4)_3 \times 18\ H_2O$ in 1 kg of an aqueous 1,6-hexanediamine solution (mixture 50:50% by weight) in a stirred autoclave. After filtering and washing, the crystalline reaction product is dried at 110° C./24 h and calcined at 500° C./24 h. This aluminosilicate zeolite contains 91.6% by weight of $SiO_2$ and 4.6% by weight of $Al_2O_3$.

The catalyst is molded with a molding aid into 2 mm extrudates, dried at 110° C./16 h and calcined at 500° C./24 h.

Catalyst D

Catalyst D is obtained by impregnating the extrudates of Catalyst B with an aqueous solution of cerium nitrate, drying at 130° C./2 h and calcining at 540° C./2 h. The Ce content is 2.5% by weight.

Catalyst E

The iron silicate zeolite of the pentasil type is synthesized under hydrothermal conditions and autogenous pressure at 165° C. from 273 g of sodium silicate, dissolved in 253 g of aqueous 1,6-hexanediamine solution (mixture 50:50% by weight), and 31 g of iron sulfate, dissolved in 21 g of 96% strength sulfuric acid and 425 g of water in a stirred autoclave in the course of 4 days. The zeolite is filtered off, washed, dried at 110° C./24 h and calcined at 500° C./24 h. An iron silicate zeolite is obtained having an $SiO_2/Fe_2O_3$ ratio of 17.7 and an $Na_2O$ content of 1.2% by weight. The catalyst is extruded together with finely divided $SiO_2$ in a weight ratio of 80:20 into 2.5 mm extrudates, dried at 110° C./16 h and calcined at 500° C./24 h.

Catalyst F

Silicon aluminum phosphate (SAPO-5) is prepared from a mixture of 200 g of 98% strength phosphoric acid, 136 g of boehmite, 60 g of silica sol (30% strength), 287 g of tripropylamine and 587 g of $H_2O$. This mixture is reacted at 150° C. under autogenous pressure for 168 hours. After filtration, the crystalline product is dried at 120° C. and calcined at 500° C. SAPO-5 contains 49.8% by weight of $P_2O_5$, 33.0% by weight of $Al_2O_3$, and 6.2% by weight of $SiO_2$. SAPO-5 is molded together with an extrusion aid into 3 mm extrudates, dried at 120° C. and calcined at 500° C.

Catalyst G

Commercially available zirconium phosphate $Zr_3(PO_4)_4$ is molded in the form of a pure substance.

Catalyst H $BPO_4$ is prepared by adding 49 g of $H_3BO_3$ to a kneader together with 117 g of $H_3PO_4$ (75% strength), evaporating off excess water and molding the reaction product into 3 mm extrudates. These extrudates are dried at 100° C. and calcined at 350° C. Catalyst N contains 8.77% by weight of B and 28.3% by weight of P.

The experimental results obtained with these catalysts and the experimental conditions are given in Table 1.

It can be seen that of all the catalysts mentioned the zeolitic catalysts are most suitable for the process according to the invention.

TABLE

| Example | 1 | 2 | 3 | 4 | 5 | 6 | 7 | 8 | 9 |
|---|---|---|---|---|---|---|---|---|---|
| Starting material | Tetramethylene diformate | | | | 1-Methyltrimethylene diformate | | | | |
| Catalyst | | C | C | A | A | B | C | D | E |
| Temperature [°C.] | 300 | 200 | 300 | 200 | 300 | 300 | 300 | 300 | 300 |
| WHSV $h^{-1}$ | 4 | 4.5 | 3 | 2.5 | 4 | 4 | 3 | 4 | 4 |
| Conversion [%] | 34.6 | 21.5 | 95.0 | 12.0 | 50.6 | 59.3 | 65.4 | 61.2 | 44.1 |
| Selectivity [%] Unsaturated ester | 83.8 | 65.1 | 93.3 | 66.7 | 89.9 | 88.5 | 82.7 | 90.5 | 77.8 |

| Example | 10 | 11 | 12 | 13 | 14 | 15 | 16 | 17 | 18 | 19 |
|---|---|---|---|---|---|---|---|---|---|---|
| Starting material | 1,6-Hexanediol acetate | | | | | | | Tetramethylene diacetate | | |
| Catalyst | A | C | C | D | F | G | H | A | E | E |
| Temperature [°C.] | 300 | 300 | 400 | 300 | 300 | 300 | 300 | 400 | 300 | 400 |
| WHSV $h^{-1}$ | 4 | 2 | 4 | 4 | 2 | 2 | 2 | 3 | 3 | 3 |
| Conversion [%] | 22.9 | 58.9 | 77.8 | 49.4 | 33.2 | 42.7 | 27.9 | 71.0 | 16.8 | 100 |
| Selectivity [%] Unsaturated ester | 86.9 | 79.5 | 78.3 | 69.4 | 78.1 | 76.3 | 81.2 | 83.9 | 96.4 | 80.8 |

Simultaneous and secondary products are for example butadiene, CO, $CO_2$, $H_2O$, formic acid, acetic acid and acetone.

We claim:
1. A process for preparing an unsaturated monoester of the formula (I)

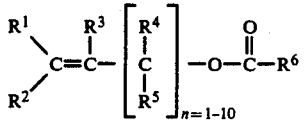 (I)

comprising reacting a diester of the formula (II)

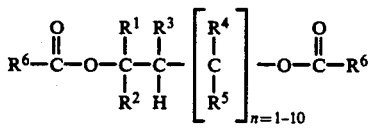 (II)

where the radicals $R^1$ to $R^5$ are identical to or different from each other and each is hydrogen, straight-chain or branched alkyl or alkenyl of from 1 to 8 carbon atoms, cycloalkyl or cycloalkenyl of from 5 to 8 carbon atoms, phenyl, benzyl, tolyl, phenylethyl, p-methylbenzyl or p-propylphenyl and $R^6$ is hydrdogen or alkyl of from 1 to 6 carbon atoms, in the presence of a catalyst, said catalyst being selected from the group consisting of zeolites in their acidic form, a phosphate of the element B, Al, Zr, Ce, Fe or Sr and mixtures thereof, thereby eliminating a carboxyl group $R^6COOH$ so as to convert the diester of the formula (II) to the unsaturated monester of the formula (I).

2. The process of claim 1, wherein an acetoxybutyl acetate, an acetoxyhexyl acetate or an acetoxyoctyl acetate is converted.

3. The process of claim 1, wherein the catalyst used is an aluminosilicate zeolite and/or an iron silicate zeolite of the pentasil type.

4. The process of claim 1, wherein the catalyst used is a zeolite of the faujasite type.

5. The process of claim 1, wherein a zeolite doped with an alkali metal, a transition metal or a rare earth metal is used as the catalyst.

6. The process of claim 1, wherein the catalyst used is selected from the group consisting of a phosphate of the element B, Al, Zr, Ce, Fe or Sr and mixtures thereof.

7. The process of claim 1, wherein the reaction is carried out in the gas phase.

8. The process of claim 1, wherein the catalyst used is selected from the group consisting of aluminum phosphates, silicon aluminum phosphates, silicon iron aluminum phosphates, cerium phosphate, zirconium phosphates, boron phosphate, iron phosphate and mixtures thereof.

9. The process of claim 6, wherein said catalyst is an aluminum phosphate which has been hydrothermally synthesized.

* * * * *